(12) United States Patent
Determan et al.

(10) Patent No.: US 9,693,950 B2
(45) Date of Patent: Jul. 4, 2017

(54) AQUEOUS FORMULATIONS FOR COATING MICRONEEDLE ARRAYS

(75) Inventors: Amy S. Determan, Woodbury, MN (US); Peter R. Johnson, Eagan, MN (US); Joan T. Moseman, Lake Elmo, MN (US); Ryan T. Woldt, Minneapolis, MN (US); Kristen J. Hansen, Afton, MN (US)

(73) Assignee: 3M INNOVATIVE PROPERTIES COMPANY, Saint Paul, MN (US)

(*) Notice: Subject to any disclaimer, the term of this patent is extended or adjusted under 35 U.S.C. 154(b) by 973 days.

(21) Appl. No.: 13/699,805

(22) PCT Filed: May 26, 2011

(86) PCT No.: PCT/US2011/038029
§ 371 (c)(1),
(2), (4) Date: Jan. 18, 2013

(87) PCT Pub. No.: WO2011/150144
PCT Pub. Date: Dec. 1, 2011

(65) Prior Publication Data
US 2013/0123707 A1    May 16, 2013

Related U.S. Application Data

(60) Provisional application No. 61/349,317, filed on May 28, 2010.

(51) Int. Cl.
| | |
|---|---|
| A61K 9/00 | (2006.01) |
| A61K 47/32 | (2006.01) |
| A61K 47/36 | (2006.01) |
| A61K 47/38 | (2006.01) |
| A61M 37/00 | (2006.01) |
| A61K 47/10 | (2017.01) |
| A61K 47/18 | (2017.01) |
| A61K 47/22 | (2006.01) |
| A61K 47/26 | (2006.01) |

(52) U.S. Cl.
CPC ............ *A61K 9/0021* (2013.01); *A61K 47/32* (2013.01); *A61K 47/36* (2013.01); *A61K 47/38* (2013.01); *A61M 37/0015* (2013.01); *A61K 47/10* (2013.01); *A61K 47/183* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,881,203 B2 | 4/2005 | Delmore et al. | |
| 2002/0128599 A1 | 9/2002 | Cormier et al. | |
| 2004/0049150 A1 | 3/2004 | Dalton et al. | |
| 2004/0265354 A1 | 12/2004 | Ameri et al. | |
| 2005/0106227 A1 | 5/2005 | Zalipsky et al. | |
| 2005/0261631 A1 | 11/2005 | Clarke et al. | |
| 2006/0195067 A1 | 8/2006 | Wolter et al. | |
| 2007/0166531 A1* | 7/2007 | Ohnishi | .................. C09C 1/043 428/323 |
| 2009/0017210 A1* | 1/2009 | Andrianov | ........ A61M 37/0015 427/256 |
| 2010/0030100 A1* | 2/2010 | Tokumoto | .......... A61B 10/0035 600/556 |

FOREIGN PATENT DOCUMENTS

| | | | |
|---|---|---|---|
| EP | 1 301 238 | 4/2003 | |
| EP | 2 153 863 | 2/2010 | |
| WO | WO 2006/138719 | 12/2006 | |
| WO | WO 2006138719 A2 * | 12/2006 | ........... A61K 9/0021 |
| WO | WO 2010/042996 | 4/2010 | |
| WO | WO 2010/059605 | 5/2010 | |
| WO | WO 2010/117602 | 10/2010 | |
| WO | WO 2011/075569 | 6/2011 | |
| WO | WO 2004/009172 | 1/2016 | |

OTHER PUBLICATIONS

"Critical Surface Tension and Contact Angle with Water for Various Polymers." *Diversified Enterprises.* 2014, https:/www.accudynetest.com/polytable_03_print.html?sortby=contact_angle. Accessed Jan. 4, 2017.
Förch, Renate, Holger Schönherr, and A. Tobias A. Jenkins, eds. *Surface Design: Applications in Bioscience and Nanotechnology*, p. 471. Weinheim: WILEY-VCH Verlag GmbH & Co. KGaA, 2009. Print. "Appendix C—Contact Angle Goniometry".
Slepička et al. 2013. *eXPRESS Polymer Letters*. 7(6):535-545. "Surface characterization of plasma treated polymers for applications as biocompatible carriers".
Yasuda et al. 1994. *Langmuir*. 10:2435-2439. "Contact Angle of Water on Polymer Surfaces".
Zhou, X., ed. May 2002. *China Logistics Publishing House*. 1st ed. pp. 521-529. "Handbook on Synthetic Resin Novel Materials".
Zhou, X., ed. Jun. 2008. *China Textile & Apparel Press*. 1st ed. pp. 306-316. "Engineering Plastic Trademark and Production Formula".

* cited by examiner

*Primary Examiner* — Susan Tran
(74) *Attorney, Agent, or Firm* — 3M Innovative Properties Company; Eric E. Silverman

(57) ABSTRACT

Aqueous formulations that include at least one active pharmaceutical ingredient; and at least one excipient, wherein the aqueous formulation has a viscosity of from 500 to 30,000 centipoise when measured at a shear rate of 100 s$^{-1}$ and a temperature of 25° C.; a surface tension that is not greater than 60 dynes/cm when measured under ambient conditions; or a contact angle on a medical grade polymeric material of 50° or greater when measured under ambient conditions. Methods of coating and coated microneedle arrays using the aqueous formulations are also disclosed herein.

17 Claims, 2 Drawing Sheets

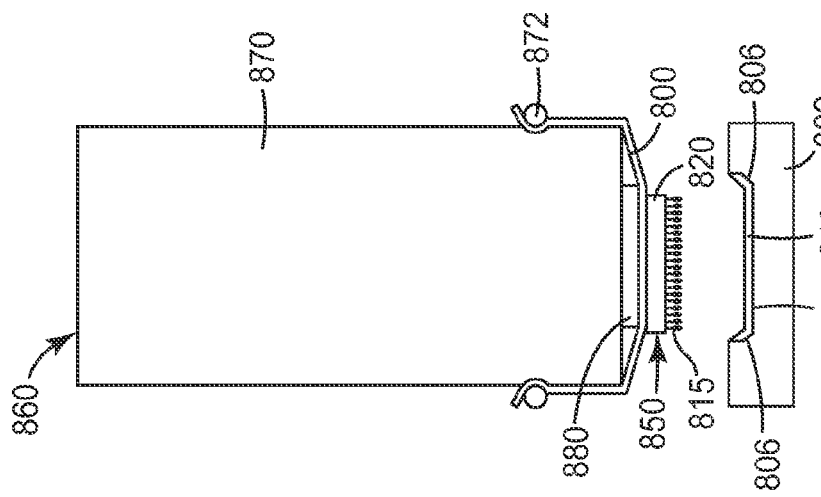
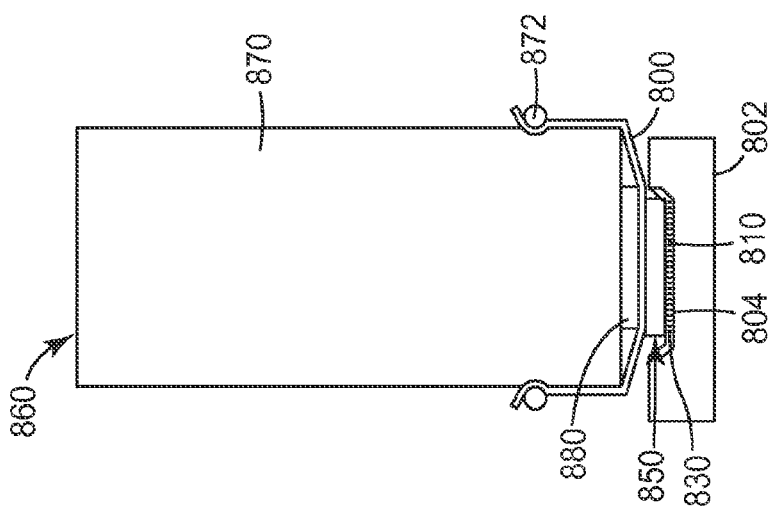
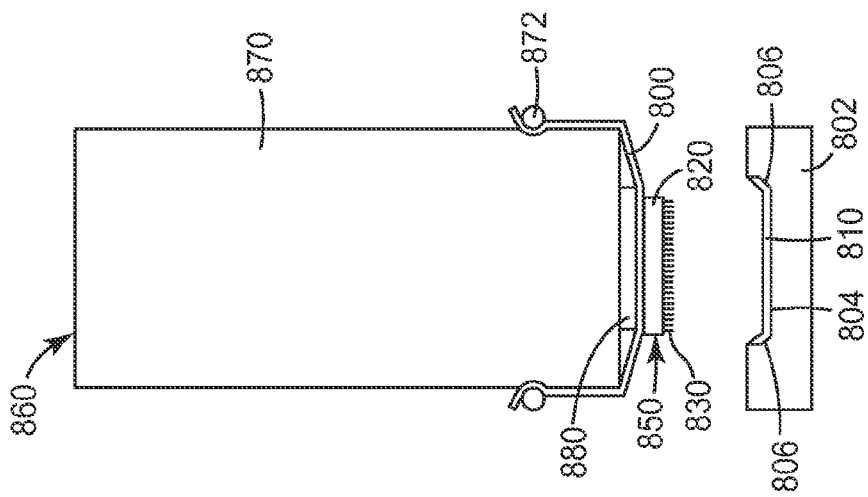

AQUEOUS FORMULATIONS FOR COATING MICRONEEDLE ARRAYS

CROSS REFERENCE TO RELATED APPLICATIONS

This application is a national stage filing under 35 U.S.C. 371 of PCT/038029, filed May 26, 2011, which claims priority to U.S. Provisional Application No. 61/349,317, filed May 28, 2010, the disclosure of which is incorporated by reference in its entirety herein.

FIELD

The present disclosure relates to formulations that are useful in coating microneedle arrays.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Microneedle devices having a fluid reservoir and conduits through which a therapeutic substance may be delivered to the skin have been proposed, but there remain a number of difficulties with such systems, such as the ability to make very fine channels that can reliably be used for fluid flow.

Microneedle devices having a dried coating on the surface of a microneedle array have desirable features compared to fluid reservoir devices. The devices are generally simpler and can directly introduce a therapeutic substance into the skin without the need for providing reliable control of fluid flow through very fine channels in the microneedle device.

BRIEF SUMMARY

Disclosed herein are aqueous formulations that include at least one active pharmaceutical ingredient; and at least one excipient, wherein the aqueous formulation has a viscosity of from 500 to 30,000 centipoise when measured at a shear rate of 100 $s^{-1}$ and a temperature of 25° C.

Disclosed herein are aqueous formulations that include at least one active pharmaceutical ingredient; and at least one excipient, wherein the aqueous formulation has a surface tension that is not greater than 60 dynes/cm when measured under ambient conditions.

Disclosed herein are aqueous formulations that include at least one active pharmaceutical ingredient; and at least one excipient, wherein the aqueous formulation has a contact angle on a medical grade polymeric material of 50° or greater when measured under ambient conditions.

Also disclosed is a method of forming a coated microneedle array, the method includes providing a microneedle array that includes a microneedle substrate and a plurality of microneedles; providing a coating substrate; providing an aqueous formulation as disclosed herein; applying the aqueous formulation to the coating substrate; bringing the aqueous formulation and the microneedles of the microneedle array into contact with one another; removing the microneedles from the aqueous formulation; and allowing at least a portion of the aqueous formulation to evaporate.

Also disclosed herein are coated microneedle arrays that include a plurality of microneedles; and a coating composition on the plurality of microneedles, the coating composition formed from aqueous formulations disclosed herein.

The subject matter of the present disclosure, in its various combinations, either in apparatus or method form, may include the following list of embodiments:

1. An aqueous formulation comprising:
   at least one active pharmaceutical ingredient; and
   at least one excipient,
   wherein the aqueous formulation has a viscosity of from 500 to 30,000 centipoise when measured at a shear rate of 100 $s^{-1}$ and a temperature of 25° C.
2. The aqueous formulation according to embodiment 1, wherein the viscosity is from 500 to 10,000 centipoise when measured at a shear rate of 100 $s^{-1}$ and a temperature of 25° C.
3. The aqueous formulation according to embodiment 1, wherein the viscosity is from 500 to 8,000 centipoise when measured at a shear rate of 100 $s^{-1}$ and a temperature of 25° C.
4. The aqueous formulation according to any one of embodiments 1 to 3, wherein the at least one active pharmaceutical ingredient is selected from vaccines, proteins, peptides, and polynucleotide sequences.
5. The aqueous formulation according to any one of embodiments 1 to 4, wherein the at least one excipient comprises a buffer.
6. The aqueous formulation according to embodiment 5, wherein the at least one buffer is selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.
7. The aqueous formulation according to any one of embodiments 5 to 6, wherein the at least one buffer is phosphate buffered saline (PBS).
8. The aqueous formulation according to any one of embodiments 1 to 7, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dihydrate or combinations thereof.
9. The aqueous formulation according to any one of embodiments 1 to 8, wherein the active pharmaceutical ingredient is a vaccine and the aqueous formulation further comprises one or more adjuvants.
10. The aqueous formulation according to any one of embodiments 1 to 9, wherein the formulation has a solids content of 5% to 80% by weight.
11. The aqueous formulation according to any one of embodiments 1 to 10, wherein the formulation has a solids content of 50% to 70% by weight.
12. The aqueous formulation according to any one of embodiments 1 to 11, wherein the formulation has from 0.01% to 70% by weight of the active pharmaceutical ingredient.
13. A method of forming a coated microneedle array comprising providing a microneedle array comprising a microneedle substrate and a plurality of microneedles;
providing a coating substrate;
providing an aqueous formulation according to any one of embodiments 1 to 12;
applying the aqueous formulation to the coating substrate;
bringing the aqueous formulation and the microneedles of the microneedle array into contact with one another;
removing the microneedles from the aqueous formulation; and
allowing at least a portion of the aqueous formulation to evaporate.

14. The method according to embodiment 13, wherein the microneedle array is configured within a patch.

15. The method according to embodiment 13, wherein the microneedle array is configured within a delivery device.

16. The method according to any one of embodiments 13 to 15, wherein the microneedle material is a medical grade polymer.

17. The method according to any one of embodiments 13 to 16, wherein the material comprising the microneedle array is selected from polycarbonate and liquid crystalline polymer.

18. The method according to any one of embodiments 13 to 17, wherein the plurality of microneedles have an average length of from 1 to 1200 micrometers and an aspect ratio of at least 2:1.

19. The method according to any one of embodiments 13 to 17, wherein the plurality of microneedles have an average length of from 1 to 1200 micrometers and an aspect ratio of at least 3:1.

20. The method according to any one of embodiments 13 to 19, wherein the plurality of microneedles have an average length of from 200 to 750 micrometers.

21. The method according to any one of embodiments 13 to 20, wherein the coating substrate is at least a portion of a coating well.

22. The method according to embodiment 21, wherein the microneedles contact the bottom surface of the coating well.

23. The method according to any one of embodiments 13 to 22, wherein the step of applying the aqueous formulation to the coating substrate comprises applying an excess of aqueous formulation to the coating substrate and adjusting the amount of aqueous formulation on the coating substrate.

24. The method according to embodiment 23, wherein adjusting the amount of aqueous formulation on the coating substrate comprises removing some aqueous formulation using an edge device.

25. The method according to any one of embodiments 13 to 24, wherein the step of bringing the aqueous formulation and the microneedles of the microneedle array into contact with one another is accomplished by moving the microneedles into contact with the aqueous formulation, by moving the aqueous formulation into contact with the microneedles, or by a combination thereof.

26. The method according to any one of embodiments 13 to 25, wherein the step of bringing the aqueous formulation and the microneedles of the microneedle array into contact with one another is repeated at least once.

27. A coated microneedle array comprising:
a plurality of microneedles; and
a coating composition on the plurality of microneedles, the coating composition formed from an aqueous formulation according to any one of embodiments 1 to 12.

28. The microneedle array according to embodiment 27, wherein the microneedle material is a medical grade polymer.

29. The microneedle array according to any one of embodiments 27 or 28, wherein the microneedle material is selected from polycarbonate and liquid crystalline polymer.

30. The microneedle array according to any one of embodiments 27 to 29, wherein the plurality of microneedles have an average length of from 1 to 1200 micrometers and an aspect ratio of at least 2:1.

31. The microneedle array according to any one of embodiments 27 to 29, wherein the plurality of microneedles have an average length of from 1 to 1200 micrometers and an aspect ratio of at least 3:1.

32. The microneedle array according to any one of embodiments 27 to 31, wherein the plurality of microneedles have an average length of from 200 to 750 micrometers.

33. An aqueous formulation comprising:
at least one active pharmaceutical ingredient; and
at least one excipient,
wherein the aqueous formulation has a surface tension that is not greater than 60 dynes/cm when measured under ambient conditions.

34. The aqueous formulation according to embodiment 33, wherein the surface tension is not greater than 55 dynes/cm.

35. The aqueous formulation according to embodiment 33, wherein the surface tension is from 40 to 55 dynes/cm.

36. The aqueous formulation according to any one of embodiments 33 to 35, wherein the at least one active pharmaceutical ingredient is selected from vaccines, proteins, peptides, and polynucleotide sequences.

37. The aqueous formulation according to any one of embodiments 33 to 36, wherein the at least one excipient comprises a buffer.

38. The aqueous formulation according to embodiment 37, wherein the at least one buffer is selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

39. The aqueous formulation according to any one of embodiments 37 or 38, wherein the at least one buffer is phosphate buffered saline (PBS).

40. The aqueous formulation according to any one of embodiments 33 to 39, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dihydrate or combinations thereof.

41. The aqueous formulation according to any one of embodiments 33 to 40, wherein the active pharmaceutical ingredient is a vaccine and the formulation further comprises one or more adjuvants.

42. The aqueous formulation according to any one of embodiments 33 to 41, wherein the formulation has a solids content of 5% to 80% by weight.

43. The aqueous formulation according to any one of embodiments 33 to 42, wherein the formulation has a solids content of 50% to 70% by weight.

44. The aqueous formulation according to any one of embodiments 33 to 43, wherein the formulation has from 0.01% to 70% by weight of the active pharmaceutical ingredient.

45. A method of forming a microneedle array comprising
providing a microneedle array comprising a microneedle substrate and a plurality of microneedles;

providing a coating substrate;
providing an aqueous formulation according to any one of embodiments 33 to 44;
applying the aqueous formulation to the coating substrate;
bringing the aqueous formulation and the microneedles of the microneedle array into contact with one another;
removing the microneedles from the aqueous formulation; and
allowing at least a portion of the aqueous formulation to evaporate.

46. The method according to embodiment 45, wherein the microneedle array is configured within a patch.

47. The method according to embodiment 45, wherein the microneedle array is configured within a delivery device.

48. The method according to any one of embodiments 45 to 47, wherein the microneedle material is a medical grade polymer.

49. The method according to any one of embodiments 45 to 48, wherein the microneedle material is selected from polycarbonate and liquid crystalline polymer.

50. The method according to any one of embodiments 45 to 49, wherein the plurality of microneedles have an average length of from 1 to 1200 micrometers and an aspect ratio of at least 2:1.

51. The method according to any one of embodiments 45 to 49, wherein the plurality of microneedles have an average length of from 1 to 1200 micrometers and an aspect ratio of at least 3:1.

52. The method according to any one of embodiments 45 to 51, wherein the plurality of microneedles have an average length of from 200 to 750 micrometers.

53. The method according to any one of embodiments 45 to 52, wherein the coating substrate is at least a portion of a coating well.

54. The method according to embodiment 53, wherein the microneedles contact the bottom surface of the coating well.

55. The method according to any one of embodiments 45 to 54, wherein the step of applying the aqueous formulation to the coating substrate comprises applying an excess of aqueous formulation to the coating substrate and adjusting the amount of aqueous formulation on the coating substrate.

56. The method according to embodiment 55, wherein adjusting the amount of aqueous formulation on the coating substrate comprises removing some aqueous formulation using an edge device.

57. The method according to any one of embodiments 45 to 56, wherein the step of bringing the aqueous formulation and the microneedles of the microneedle array into contact with one another is accomplished by moving the microneedles into contact with the aqueous formulation, by moving the aqueous formulation into contact with the microneedles, or by a combination thereof.

58. The method according to any one of embodiments 45 to 57, wherein the step of bringing the aqueous formulation and the microneedles of the microneedle array into contact with one another is repeated at least once.

59. A coated microneedle array comprising:
a plurality of microneedles; and
a coating composition on the plurality of microneedles, the coating composition formed from an aqueous formulation according to any one of embodiments 33 to 44.

60. The microneedle array according to embodiment 59, wherein the microneedle material is a medical grade polymer.

61. The microneedle array according to any one of embodiments 59 or 60, wherein the microneedle material is selected from polycarbonate and liquid crystal polymer.

62. The microneedle array according to any one of embodiments 59 to 61, wherein the plurality of microneedles have an average length of from 1 to 1200 micrometers and an aspect ratio of at least 2:1.

63. The microneedle array according to any one of embodiments 59 to 61, wherein the plurality of microneedles have an average length of from 1 to 1200 micrometers and an aspect ratio of at least 3:1.

64. The microneedle array according to any one of embodiments 59 to 63, wherein the plurality of microneedles have an average length of from 200 to 750 micrometers.

65. An aqueous formulation comprising:
at least one active pharmaceutical ingredient; and
at least one excipient,
wherein the aqueous formulation has a contact angle on a medical grade polymeric material of 50° or greater when measured under ambient conditions.

66. The aqueous formulation according to embodiment 65, wherein the contact angle on a medical grade polymeric material is 55° or greater.

67. The aqueous formulation according to embodiment 65, wherein the contact angle on a medical grade polymeric material is 65° or greater.

68. The aqueous formulation according to any one of embodiments 65 to 67, wherein the at least one active pharmaceutical ingredient is selected from vaccines, proteins, peptides, and polynucleotide sequences.

69. The aqueous formulation according to any one of embodiments 65 to 68, wherein the at least one excipient comprises a buffer.

70. The aqueous formulation according to embodiment 69, wherein the at least one buffer is selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

71. The aqueous formulation according to any one of embodiments 69 or 70, wherein the at least one buffer is phosphate buffered saline (PBS).

72. The aqueous formulation according to any one of embodiments 65 to 71, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dihydrate or combinations thereof.

73. The aqueous formulation according to any one of embodiments 65 to 72, wherein the active pharmaceutical ingredient is a vaccine and the aqueous formulation further comprises one or more adjuvants.

74. The aqueous formulation according to any one of embodiments 65 to 73, wherein the formulation has a solids content of 5% to 80% by weight.

75. The aqueous formulation according to any one of embodiments 65 to 74, wherein the formulation has a solids content of 50% to 70% by weight.

76. The aqueous formulation according to any one of embodiments 65 to 75, wherein the formulation has from 0.01% to 70% by weight of the active pharmaceutical ingredient.

77. A method of forming a microneedle array comprising
providing a microneedle array comprising a microneedle substrate and a plurality of microneedles;
providing a coating substrate;

providing an aqueous formulation according to any one of embodiments 65 to 76;

applying the aqueous formulation to the coating substrate;

bringing the aqueous formulation and the microneedles of the microneedle array into contact with one another; removing the microneedles from the aqueous formulation; and allowing at least a portion of the aqueous formulation to evaporate.

78. The method according to embodiment 77, wherein the microneedle array is configured within a patch.

79. The method according to embodiment 77, wherein the microneedle array is configured within a delivery device.

80. The method according to any one of embodiments 77 to 79, wherein the microneedle material is a medical grade polymer.

81. The method according to any one of embodiments 77 to 80, wherein the microneedle material is selected from polycarbonate and liquid crystalline polymer.

82. The method according to any one of embodiments 77 to 81, wherein the plurality of microneedles have an average length of from 1 to 1200 micrometers and an aspect ratio of at least 2:1.

83. The method according to any one of embodiments 77 to 81, wherein the plurality of microneedles have an average length of from 1 to 1200 micrometers and an aspect ratio of at least 3:1.

84. The method according to any one of embodiments 77 to 83, wherein the plurality of microneedles have an average length of from 200 to 750 micrometers.

85. The method according to any one of embodiments 77 to 84, wherein the coating substrate is at least a portion of a coating well.

86. The method according to embodiment 85, wherein the microneedles contact the bottom surface of the coating well.

87. The method according to any one of embodiments 77 to 86, wherein the step of applying the aqueous formulation to the coating substrate comprises applying an excess of aqueous formulation to the coating substrate and adjusting the amount of aqueous formulation on the coating substrate.

88. The method according to embodiment 87, wherein adjusting the amount of aqueous formulation on the coating substrate comprises removing some aqueous formulation using an edge device.

89. The method according to any one of embodiments 77 to 88, wherein the step of bringing the aqueous formulation and the microneedles of the microneedle array into contact with one another is accomplished by moving the microneedles into contact with the aqueous formulation, by moving the aqueous formulation into contact with the microneedles, or by a combination thereof.

90. The method according to any one of embodiments 77 to 89, wherein the step of bringing the aqueous formulation and the microneedles of the microneedle array into contact with one another is repeated at least once.

91. A coated microneedle array comprising:

a plurality of microneedles; and a coating composition on the plurality of microneedles, the coating composition formed from an aqueous formulation according to any one of embodiments 65 to 76.

92. The microneedle array according to embodiment 91, wherein the microneedle material is a medical grade polymer.

93. The microneedle array according to any one of embodiments 91 or 92, wherein the microneedle material is selected from polycarbonate and liquid crystalline polymer.

94. The microneedle array according to any one of embodiments 91 to 93, wherein the plurality of microneedles have an average length of from 1 to 1200 micrometers and an aspect ratio of at least 2:1.

95. The microneedle array according to any one of embodiments 91 to 93, wherein the plurality of microneedles have an average length of from 1 to 1200 micrometers and an aspect ratio of at least 3:1.

96. The microneedle array according to any one of embodiments 91 to 95, wherein the plurality of microneedles have an average length of from 200 to 750 micrometers.

97. A coated microneedle array comprising:

a plurality of microneedles comprising a microneedle material and having a length of from 1 to 1200 micrometers and an aspect ratio of at least 3:1; and a coating composition on the plurality of microneedles, the coating composition formed from an aqueous formulation, the aqueous formulation comprising:

at least one active pharmaceutical ingredient; and at least one excipient, wherein the aqueous formulation has a contact angle on the microneedle material of 50° or greater when measured at ambient conditions.

98. The coated microneedle array according to embodiment 97, wherein the contact angle on a medical grade polymeric material is 55° or greater.

99. The coated microneedle array according to embodiment 97, wherein the contact angle on a medical grade polymeric material is 65° or greater.

100. The coated microneedle array according to any one of embodiments 97 to 99, wherein the at least one active pharmaceutical ingredient is selected from vaccines, proteins, peptides, and polynucleotide sequences.

101. The coated microneedle array according to any one of embodiments 97 to 100, wherein the at least one excipient comprises a buffer.

102. The coated microneedle array according to embodiment 101, wherein the at least one buffer is selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

103. The coated microneedle array according to any one of embodiments 101 to 102, wherein the at least one buffer is phosphate buffered saline (PBS).

104. The coated microneedle array according to any one of embodiments 97 to 103, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dihydrate or combinations thereof.

105. The coated microneedle array according to any one of embodiments 97 to 104, wherein the active pharmaceutical ingredient is a vaccine and the aqueous formulation further comprises one or more adjuvants.

106. The coated microneedle array according to any one of embodiments 97 to 105, wherein the formulation has a solids content of 5% to 80% by weight.

107. The coated microneedle array according to any one of embodiments 97 to 106, wherein the formulation has a solids content of 50% to 70% by weight.

108. The coated microneedle array according to any one of embodiments 97 to 107, wherein the formulation has from 0.01% to 70% by weight of the active pharmaceutical ingredient.

109. A method of forming a coated microneedle array comprising
providing a microneedle array comprising a microneedle substrate and a plurality of microneedles;
providing a coating substrate;
providing an aqueous formulation comprising at least one active pharmaceutical ingredient and at least one excipient, wherein the aqueous formulation has a viscosity of from 500 to 30,000 centipoise when measured at a shear rate of 100 s$^{-1}$ and a temperature of 25° C.;
applying the aqueous formulation to the coating substrate;
bringing the aqueous formulation and the microneedles of the microneedle array into contact with one another;
removing the microneedles from the aqueous formulation; and
allowing at least a portion of the aqueous formulation to evaporate.

110. The method according to embodiment 109, wherein the viscosity is from 500 to 10,000 centipoise when measured at a shear rate of 100 s$^{-1}$ and a temperature of 25° C.

111. The method according to embodiment 109, wherein the viscosity is from 500 to 8,000 centipoise when measured at a shear rate of 100 s$^{-1}$ and a temperature of 25° C.

112. The method according to any one of embodiments 109 to 111, wherein the aqueous formulation has a contact angle on a medical grade polymeric material of 50° or greater when measured under ambient conditions.

113. The method according to any one of embodiments 109 to 111, wherein the aqueous formulation has a contact angle on a medical grade polymeric material of 65° or greater when measured under ambient conditions.

114. A method of forming a coated microneedle array comprising
providing a microneedle array comprising a microneedle substrate and a plurality of microneedles;
providing a coating substrate;
providing an aqueous formulation comprising at least one active pharmaceutical ingredient and at least one excipient, wherein the aqueous formulation has a contact angle on a medical grade polymeric material of 50° or greater when measured under ambient conditions;
applying the aqueous formulation to the coating substrate;
bringing the aqueous formulation and the microneedles into contact with one another;
removing the microneedles from the aqueous formulation; and
allowing at least a portion of the aqueous formulation to evaporate.

115. The method according to embodiment 114, wherein the contact angle on a medical grade polymeric material is 65° or greater when measured under ambient conditions.

116. The method according to any one of embodiments 109 to 115, wherein the at least one active pharmaceutical ingredient is selected from vaccines, proteins, peptides, and polynucleotide sequences.

117. The method according to any one of embodiments 109 to 116, wherein the at least one excipient comprises a buffer selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

118. The method according to any one of embodiments 109 to 117, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dehydrate, or combinations thereof.

119. The method according to any one of embodiments 109 to 118, wherein the active pharmaceutical ingredient is a vaccine and the aqueous formulation further comprises one or more adjuvants.

120. The method according to any one of embodiments 109 to 119, wherein the material comprising the microneedle array is selected from polycarbonate and liquid crystalline polymer.

121. The method according to any one of embodiments 109 to 120, wherein the coating substrate is at least a portion of a coating well.

122. The method according to embodiment 121, wherein the coating well comprises a bottom surface and the microneedles contact the bottom surface of the coating well.

123. The method according to any one of embodiments 109 to 122, wherein the step of applying the aqueous formulation to the coating substrate comprises applying an excess of aqueous formulation to the coating substrate and adjusting the amount of aqueous formulation on the coating substrate.

124. The method according to embodiment 123, wherein the step of adjusting the amount of aqueous formulation on the coating substrate comprises removing some aqueous formulation using an edge device.

125. The method according to any one of embodiments 109 to 124, wherein the step of bringing the aqueous formulation and the microneedles of the microneedle array into contact with one another is repeated at least once.

126. The method according to any one of embodiments 109 to 125, wherein the aqueous formulation has a surface tension that is from 40 and 55 dynes/cm when measured under ambient conditions.

127. A coated microneedle array comprising:
a plurality of microneedles; and
a coating composition on the plurality of microneedles, the coating composition formed from an aqueous formulation comprising at least one active pharmaceutical ingredient and at least one excipient, wherein the aqueous formulation has a viscosity of from 500 to 30,000 centipoise when measured at a shear rate of 100 s$^{-1}$ and a temperature of 25° C.

128. The microneedle array according to embodiment 127, wherein the viscosity is from 500 to 10,000 centipoise when measured at a shear rate of 100 s$^{-1}$ and a temperature of 25° C.

129. The microneedle array according to embodiment 127, wherein the viscosity is from 500 to 8,000 centipoise when measured at a shear rate of 100 s$^{-1}$ and a temperature of 25° C.

130. The microneedle array according to any one of embodiments 127 to 129, wherein the aqueous formulation has a contact angle on a medical grade polymeric material of 50° or greater when measured under ambient conditions.

131. The microneedle array according to any one of embodiments 127 to 129, wherein the aqueous formulation has a contact angle on a medical grade polymeric material of 65° or greater when measured under ambient conditions.

132. A coated microneedle array comprising:
a plurality of microneedles; and
a coating composition on the plurality of microneedles, the coating composition formed from an aqueous formulation comprising at least one active pharmaceutical ingredient and at least one excipient, wherein the aqueous formulation has a contact angle on a medical grade polymeric material of 50° or greater when measured under ambient conditions.

133. The microneedle array according to embodiment 132, wherein the aqueous formulation has a contact angle on a medical grade polymeric material of 65° or greater when measured under ambient conditions.

134. The microneedle array according to any one of embodiments 127 to 133, wherein the at least one active pharmaceutical ingredient is selected from vaccines, proteins, peptides, and polynucleotide sequences.

135. The microneedle array according to any one of embodiments 127 to 134, wherein the at least one excipient comprises a buffer selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

136. The microneedle array according to any one of embodiments 127 to 135, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dehydrate, or combinations thereof.

137. The microneedle array according to any one of embodiments 127 to 136, wherein the active pharmaceutical ingredient is a vaccine and the aqueous formulation further comprises one or more adjuvants.

138. The microneedle array according to any one of embodiments 127 to 137, wherein the material comprising the microneedle array is selected from polycarbonate and liquid crystalline polymer.

139. The microneedle array according to any one of any one of embodiments 127 to 138, wherein the aqueous formulation has a surface tension that is from 40 and 55 dynes/cm when measured under ambient conditions.

BRIEF DESCRIPTION OF THE DRAWINGS

The disclosure may be more completely understood in consideration of the following detailed description of various embodiments of the disclosure in connection with the accompanying drawings, in which:

FIGS. 3A, 3B, and 3C are schematic cross-sectional views depicting portions of methods disclosed herein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
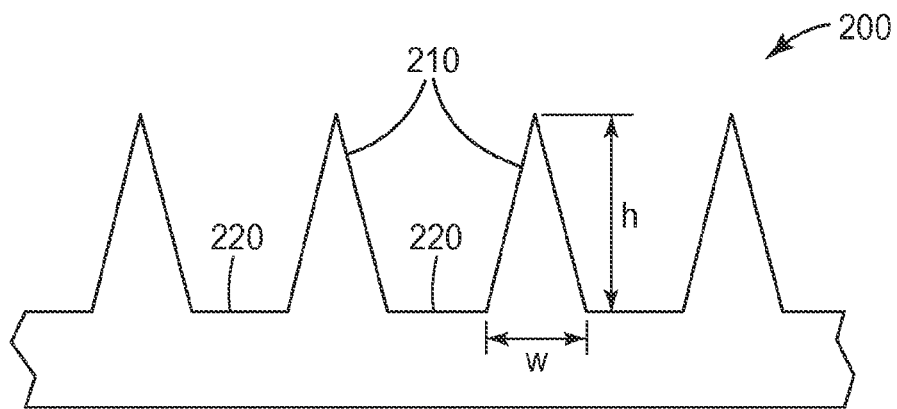
FIG. 1 is a schematic cross-sectional view of an uncoated microneedle array.

In the following description, reference is made to the accompanying drawing that forms a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified.

The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g., 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Disclosed herein are formulations that can be utilized to coat microneedle arrays. The formulations can be aqueous and can be referred to as aqueous formulations, aqueous compositions, or coating formulations.

Aqueous formulations disclosed herein generally include water as a solvent. Generally, the solvent composition in an aqueous formulation is selected such that it may dissolve or disperse the active pharmaceutical ingredient and excipients. Aqueous formulations disclosed herein can also include co-solvents in addition to water. In embodiments, an aqueous formulation can optionally include additional solvents (also referred to as co-solvents) such as ethanol, iospropanol, methanol, propanol, butanol, propylene glycol, dimethysulfoxide, glycerin, 1-methyl-2-pryrrolidinone, or N,N-dimethylformamide Aqueous formulations disclosed herein generally include at least one active pharmaceutical ingredient (referred to herein as an "API"); and at least one excipient. Aqueous formulations can also include additional components, such as a second (or subsequent) API, a second (or subsequent) excipient, components not noted herein, or some combination thereof.

The at least one API can generally include any pharmacologically active component. The at least one API can include vaccines, hormones, proteins, peptides, lipoproteins, glycoproteins, polysaccharides, lipopolysaccharides, oligosaccharides, glycolipids, polynucleotide sequences, DNA vaccines, and antibiotics such as ceftriaxone.

The at least one API can also be a small molecule that may be otherwise difficult or impossible to deliver by passive transdermal delivery. Examples of such molecules include ionic molecules, such as bisphosphonates, for example sodium alendronate or pamedronate; molecules with physicochemical properties that are not conducive to passive transdermal delivery such as naltrexone, and lidocaine for example.

The at least one API can also include agents for dermatological treatments, vaccine delivery, or enhancement of an immune response with vaccine adjuvants. Examples of suitable vaccines include DNA vaccine, cellular vaccines such as a dendritic cell vaccine, recombinant protein vaccine, therapeutic cancer vaccine, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, polio vaccine, herpes vaccine, human papilloma virus vaccine, rotavirus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes antigens in the forms of proteins, peptides, lipoproteins, glycoproteins, polysaccharides, lipopolysaccharides, oligosaccharides, glycolipids, polynucleotide sequences, weakened or killed viruses, virus particles, virus-like particles, weakened or killed bacteria, bacterial cell walls, toxoids, and desensitizing agents such as cat, dust, or pollen allergens. Additional examples of suitable vaccines and vaccine adjuvants are described in United States Patent Application Publication Nos. 2004/0049150, 2004/0265354, and US2006/0195067, the disclosures of which are incorporated herein by reference.

In embodiments that include an API that is a vaccine, the aqueous formulation can also optionally include one or more adjuvants. An adjuvant is an agent that modifies the effect of another agent (in this case the vaccine API). Adjuvants are often utilized to enhance the recipient's immune response to the vaccine. The particular identity of the adjuvant can depend at least in part on the identity of the API vaccine. Adjuvants can include aluminum phosphate, aluminum phosphate gel, aluminum hydroxide, squalene, beta-glucan, CpG containing oligonucleotides, QS-21, glucosaminylmuramyl dipeptide (GMDP), murametide, dimethyldioctadecylammonium bromide (DDA), Quil A, threonyl-muramyl dipeptide (threonyl-MDP), MTP-PE, MTP-PE liposomes, a 4-amino-imidazo[4,5-c]quinoline based immune response modifier compound, a 4-amino[1,3]thiazolo[4,5-c]quinoline based immune response modifier compound, a TLR6 agonist, a TLR7 agonist, a TLR8 agonist, a TLR9 agonist, imiquimod, resiquimod, 2-propyl[1,3]thiazolo[4,5-c]quinolin-4-amine, IL-2, IL-4, IL-10, IL-12, IL-15, IL-18, and combinations thereof.

In embodiments, the at least one API can be a composition of matter or mixture containing a component that is pharmacologically effective when administered in an amount of less than about 5 mg, and in some embodiments less than about 0.25 mg. Examples of such high potency APIs include, for example, human growth hormone (hGH), tissue plasminogen activator (TPA), calcitonin gene related peptide (CGRP), leutinizing hormone releasing hormone (LHRH), LHRH analogs (such as goserelin, leuprolide, buserelin, triptorelin), gonadorelin, and napfarelin, menotropins (follicle stimulating hormone (FSH) and leutinizing hormone (LH)), human menopausal goanadotropins (hMG), human chorionic gonadotropin (hCG), vasopressin, desmopressin, insulin, adrenocortiocotropic hormone (ACTH), ACTH analogs such as ACTH (1-24), calcitonin, parathyroid hormone (PTH), parathyroid hormone antagonists, oxytocin, deamino [Val4, D-Arg8] arginine vasopressin, interferon alpha, interferon beta, interferon gamma, tumor necrosis factor (TNF), erythropoietin (EPO), granulocyte macrophage colony stimulating factor (GM-CSF), granulocyte colony stimulating factor (G-CSF), interleukins, IL-2 (IL-2), interleukin-10 (IL-10), glucagon, and growth hormone releasing factor (GRF)). The agents can be in various forms, such as free bases, acids, charged or uncharged molecules, components of molecular complexes or nonirritating, pharmacologically acceptable salts. Also, simple derivatives of the agents (such as ethers, esters, amides, etc) which are physiologically hydrolyzed at body pH, enzymes, etc., can be employed.

An aqueous formulation also includes at least one excipient. An excipient can function to maintain the active nature of the API, to facilitate the coating performance of the formulation, or a combination thereof. The particular excipient to be utilized can depend at least in part on the particular API (or APIs) that are included in the aqueous formulation.

Exemplary excipients can include for example buffers, carbohydrates, polymers, amino acids, polyamino acids, surfactants, proteins, non-aqueous solvents, inorganic salts, acids, bases, antioxidants and saccharin.

In embodiments, disclosed aqueous formulations can include at least one buffer as an excipient. A buffer can generally function to stabilize the pH of the aqueous formulation. The particular buffer to be utilized can depend at least in part on the particular API (or APIs) that are included in the aqueous formulation. The pH of the aqueous formulation can be important, for example, to maintain the solubility of the API at a desired level. Generally, any commonly utilized buffers can be used in disclosed aqueous formulations.

Exemplary buffers can include for example, histidine, phosphate buffers, acetate buffers, citrate buffers, glycine buffers, ammonium acetate buffers, succinate buffers, pyrophosphate buffers, Tris acetate (TA) buffers, and Tris buffers. Buffered saline solutions can also be utilized as buffers. Exemplary buffered saline solutions include, for example, phosphate buffered saline (PBS), Tris buffered saline (TBS), saline-sodium acetate buffer (SSA), saline-sodium citrate buffer (SSC). In embodiments, PBS can be utilized as the buffer.

In embodiments, aqueous formulations can include at least one carbohydrate, such as a sugar. Suitable sugars can include for example non-reducing sugars such as raffinose, stachyose, sucrose, and trehalose; and reducing sugars such as monosaccharides and disaccharides.

Exemplary monosacharides can include apiose, arabinose, digitoxose, fucose, fructose, galactose, glucose, gulose, hamamelose, idose, lyxose, mannose, ribose, tagatose, and xylose. Exemplary disaccharides can include for example cellobiose, gentiobiose, lactose, lactulose, maltose, melibiose, primeverose, rutinose, scillabiose, sophorose, turanose, and vicianose. In embodiments, sucrose, trehalose, fructose, maltose, or combinations thereof can be utilized. All optical isomers of exemplified sugars (D, L, and racemic mixtures) are also included herein.

In embodiments, aqueous formulations can include at least one carbohydrate, such as a polysaccharide. Suitable polysaccharides can include for example starches such as hydroxyethyl starch, pregelantized corn starch, pentastarch, dextrin, dextran or dextran sulfate, gamma-cyclodextrin, alpha-clycodextrin, beta-clycodextrin, glucosyl-alpha-cylcodextrin, maltosyl-alpha-cyclodextrin, glucosyl-beta-cyclodextrin, maltosyl-beta-cyclodextrin, 2-hydroxy-beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-alpha-cyclodextrin, sulfobutylether-beta-cyclodextrin, and sulfobutylether-gamma-cyclodextrin. In embodiments, hydroxyethyl starch, dextrin, dextran, gamma-cyclodextrin, beta-cyclodextrin, or combinations thereof can be utilized. In embodiments, dextrans having an average molecular mass of 35,000 to 76,000 can be utilized.

In embodiments, aqueous formulations can include at least one carbohydrate, such as a cellulose. Suitable celluloses can include for example hydroxyethyl cellulose (HEC), methyl cellulose (MC), microcrystalline cellulose, hydroxypropyl methyl cellulose (HPMC), hydroxyethylmethyl cellulose (HEMC), hydroxypropyl cellulose (HPC), and mixtures thereof.

In embodiments, aqueous formulations can include at least one polymer, such as for example, polyvinyl pyrrolidone (PVP), polyethylene glycol (PEG), polyvinyl alcohol (PVA), and polyethylene glycol sorbitan isostearate. In embodiments, polyvinyl pyrrolidones (PVP) having an average molecular weight of 10,000 can be utilized. In embodiments, polyvinyl pyrrolidones (PVP having an average molecular weight of 5,000 to 1.5 million can be utilized. In embodiments, polyethylene glycols having an average molecular weight of 300 to 8,000 can be utilized.

In embodiments, aqueous formulations can include at least one amino acid. Suitable amino acids can include for example lysine, histidine, cysteine, glutamate, lysine acetate, sarcosine, proline, threonine, asparagine, aspartic acid, glutamic acid, glutamine, isoleucine, leucine, methionine, phenylalanine, serubem tryptophan, tyrosine, valine, alanine, agrinine, and glycine. In many cases the salt form of the amino acids can be used to increase the aqueous solubility of the amino acid in the aqueous formulation.

In embodiments, aqueous formulations can include at least one polyamino acid. Suitable polyamino acids can include for example polyhistidine, polyaspartic acid, and polylysine. In embodiments, aqueous formulations can include at least one protein. Suitable proteins can include for example human serum albumin and bioengineered human albumin.

In embodiments, aqueous formulations can include at least one surfactant which can be amphoteric, cationic, anionic, or nonanionic. Suitable surfactants can include for example lecithin, polysorbates (such as polysorbate 20, polysorbate 40, and polysorbate 80 for example), glycerol, sodium lauroamphoacetate, sodium dodecyl sulfate, cetylpyridinium chloride (CPC), dodecyltrimethyl ammonium chloride (DoTAC), sodium desoxycholate, benzalkonium chloride, sorbitan laurate, and alkoxylated alcohols (such as laureth-4).

In embodiments, aqueous formulations can include at least one inorganic salt. Suitable inorganic salts can include for example sodium chloride, and potassium chloride.

A non-aqueous solvent, referred to above as a co-solvent can also be categorized as an excipient. In embodiments, aqueous formulations can include at least one non-aqueous solvent such as ethanol, iospropanol, methanol, propanol, butanol, propylene glycol, dimethysulfoxide, glycerin, 1-methyl-2-pryrrolidinone, N,N-dimethylformamide, and the like.

In embodiments, aqueous formulations can include saccharin, for example saccharin sodium dihydrate. In embodiments, aqueous formulations can include a lipid such as dipalmitoylphosphatidylcholine (DPPC) for example.

In embodiments, aqueous formulations can include at least one weak acid, weak base, strong acid, strong base, or some combination thereof. Acids and bases can serve the purpose of solubilizing or stabilizing the API. These acids and bases can be referred to as counterions. These acids and bases can be organic or inorganic. Exemplary weak acids include for example acetic acid, propionic acid, pentanoic acid, citric acid, succinic acid, glycolic acid, gluconic acid, glucuronic acid, lactic acid, malic acid, pyruvic acid, tartaric acid, tartronic acid, fumaric acid, glutamic acid, aspartic acid, malonic acid, butyric acid, crotonic acid, digylcolide acid, and glutaric acid. Exemplary strong acids include for example hydrochloric acid, hydrobromic acid, nitric acid, sulfonic acid, sulfuric acid, maleic acid, phosphoric acid, benzene sulfonic acid, and methane sulfonic acid. Exemplary weak bases include for example ammonia, morpholine, histidine, lysine, arginine, monoethanolamine, diethanolamine, triethanolamine, tromethamine, methylglucamine, and glucosamine. Exemplary strong bases include for example sodium hydroxide, potassium hydroxide, calcium hydroxide, and magnesium hydroxide.

In embodiments, aqueous formulations can include at least one antioxidant. Suitable antioxidants can include for example sodium citrate, citric acid, EDTA, ascorbic acid, methionine, sodium ascorbate, and combinations thereof.

The amounts of the various components in disclosed aqueous formulations can vary depending on the identity of the components in the aqueous formulation, the amount of API desired on the microneedle array, the type of microneedle array being coated, other considerations not discussed herein, or some combination thereof. In embodiments, disclosed aqueous formulations can have an overall solids content from 5% to 80% by weight; from 10% to 70% by weight; or from 50% to 70% by weight.

Aqueous formulations can also be characterized based on the amount of API in the formulation. In embodiments, a disclosed aqueous formulation can have from 0.01% to 80% by weight of the at least one API; or from 0.1% to 70% by weight of the at least one API. Aqueous formulations can also be characterized based on the amount of carbohydrate in the formulation. In embodiments, a disclosed aqueous formulation can have from 0% to 80% by weight of at least one carbohydrate; or from 5% to 70% by weight of at least one carbohydrate. Carbohydrates, if utilized, can be used to increase the viscosity of the aqueous formulation. Aqueous formulations can also be characterized based on the amount of polymer in the formulation. In embodiments, a disclosed aqueous formulation can have from 0% to 50% by weight of at least one polymer; or from 1% to 20% by weight of at least one polymer. Polymers, if utilized, can be used as a viscosity enhancer. Aqueous formulations can also be characterized based on the amount of surfactant in the formulation. In embodiments, a disclosed aqueous formulation can have from 0% to 10% by weight of at least one surfactant; or from 0% to 5% by weight of at least one surfactant.

Aqueous formulations disclosed herein can be further described by various properties of the formulations. Exemplary properties that can be utilized to further describe the aqueous formulations include for example, the viscosity of the aqueous formulation, the surface tension of the aqueous formulation, the contact angle of the coating composition on the material of the microneedle material, or some combination thereof.

In embodiments, an aqueous formulation can be further characterized by its viscosity. Generally, viscosity is a measurement of the resistance of a fluid which is being deformed by either shear stress or tensile stress. In embodiments, disclosed aqueous formulations can be characterized by their resistance to being deformed by a shear stress, which can also be referred to as the shear viscosity of the aqueous formulation. Various instruments can be used for viscosity testing, including rheometers. In embodiments, the viscosity of an aqueous formulation can be measured using a rheometer, for example rheometers from TA Instruments (New Castle, Del.).

Generally, if an aqueous formulation is too viscous, the aqueous formulation will be difficult to utilize in manufacturing methods, can produce non-reproducible coatings (and therefore non-reproducible amounts of API that will be administered by the microneedle array upon use) and can result in an overall reduction in the coating weight. If an aqueous formulation is not viscous enough, the aqueous formulation will not be able to effectively coat the microneedle surfaces (which could therefore require more dips of the microneedle in the aqueous formulation, thereby increasing the manufacturing costs) and in some cases capillary forces can cause the formulation to coat the microneedle and the microneedle substrate, which is sometimes referred to as "capillary jump". The desired viscosity of an aqueous formulation can depend at least in part on the geometry of the microneedles, the particular coating method being utilized, the desired number of coating steps, other considerations not discussed herein, or some combination thereof.

In embodiments, aqueous formulations disclosed herein can have a viscosity (or shear viscosity) of from 500 to 30,000 centipoise (cps) when measured at a shear rate of 100 $s^{-1}$ at a temperature of 25° C. In embodiments, aqueous formulations disclosed herein can have a viscosity (or shear viscosity) of from 500 to 10,000 cps when measured at a shear rate of 100 $s^{-1}$ at a temperature of 25° C. In embodiments, aqueous formulations disclosed herein can have a viscosity (or shear viscosity) of from 500 to 8,000 cps when measured at a shear rate of 100 $s^{-1}$ at a temperature of 25° C.

In embodiments, an aqueous formulation can be further characterized by its surface tension. Various methods can be utilized to measure surface tension. An exemplary type of surface tension measurement is based on the pendant drop method. In a pendant drop method of measuring surface tension, a drop of liquid is suspended from the end of a tube by surface tension. The force due to surface tension is proportional to the length of the boundary between the liquid and the tube. Various instruments that encompass optics systems for measuring the relevant parameters of the drop and software packages for calculating the surface tension based on the measured parameters can be utilized herein. An exemplary instrument includes the Drop Shape Analysis System (Model DSA 100S) available from Krüss (Hamburg, Germany).

Generally, if an aqueous formulation has too high a surface tension, the aqueous formulation may not be able to effectively coat the microneedle surfaces (which could therefore require more dips of the microneedle in the aqueous formulation thereby increasing the manufacturing costs), it may be difficult to get the aqueous formulation to effectively coat the microneedle, or a combination thereof. If an aqueous formulation has too low a surface tension, the aqueous formulation may undergo capillary jump, in which it not only coats the tip of the microneedle but it extends further down the microneedle towards the microneedle substrate and may in some cases actually coat the microneedle substrate. The desired surface tension of an aqueous formulation can depend at least in part on the geometry of the microneedles, the particular coating method being utilized, the desired number of coating steps, other considerations not discussed herein, or some combination thereof.

In embodiments, aqueous formulations disclosed herein can have a surface tension (measured at ambient, or room temperature conditions) that is not greater than 60 dynes/cm. In embodiments, aqueous formulations disclosed herein can have a surface tension that is not greater than 55 dynes/cm. In embodiments, aqueous formulations disclosed herein can have a surface tension from 40 dynes/cm to 55 dynes/cm.

In embodiments, an aqueous formulation can be further characterized by its contact angle with the material of the microneedles (also referred to as the "microneedle material"). It should be noted that the contact angle of the aqueous formulation with respect to the microneedle material is measured on a horizontal substrate made of the microneedle material. The microneedle material can be (or include) silicon or a metal such as stainless steel, titanium, or nickel titanium alloy. The microneedle material can also be (or include) a medical grade polymeric material. Generally, the contact angle of a disclosed aqueous formulation with the microneedle material is an indication of the affinity of the aqueous formulation for the microneedle material. The lower the contact angle is, the stronger the attraction of the aqueous formulation for the microneedle material, resulting in increased wetting of the microneedle surface. The contact angle of the aqueous formulation on the microneedle material can be measured using various methods. In embodiments, the contact angle of the aqueous formulation on the microneedle material can be measured using the sessile drop method for example. Generally, a goniometer (or an instrument that employs a goniometer) can be utilized to measure contact angles, an example of such an instrument is the Drop Shape Analysis System (Model DSA 100S) available from Krüss (Hamburg, Germany). In embodiments, the contact angle can be measured within 5 seconds of the transfer of the coating formulation onto the substrate.

Generally, if an aqueous formulation has a contact angle that is too low (the aqueous formulation is strongly attracted to the microneedle material), the aqueous formulation can produce inconsistent coatings (and therefore amounts of API on the microneedle array), or the aqueous formulation may undergo capillary jump, in which it not only coats the tip of the microneedle but it extends further down the microneedle towards the microneedle substrate and may in some cases actually coat the microneedle substrate. A contact angle that is too low can also increase the chances of capillary jump, particularly in an aqueous formulation having a low viscosity. If an aqueous formulation has a contact angle that is too high (the aqueous formulation is not strongly attracted or even repelled from the microneedle material), it may be difficult to get the aqueous formulation to effectively coat the microneedle. The desired contact angle of an aqueous formulation on the microneedle material can depend at least in part on the geometry of the microneedles, the particular coating method being utilized, the desired number of coating steps, other considerations not discussed herein, or some combination thereof.

In embodiments, aqueous formulations disclosed herein can have a contact angle (measured at ambient, or room temperature conditions) with the microneedle material of 50° or greater. In embodiments, aqueous formulations disclosed herein can have a contact angle of 55° or greater. In embodiments, aqueous formulations disclosed herein can have a contact angle of 65° or greater.

In embodiments, the microneedle material can be a medical grade polymeric material and the aqueous formulation can have a contact angle with the medical grade polymeric material of 50° or greater; 55° or greater; or 65° or greater. Exemplary types of medical grade polymeric materials include for example, polycarbonate, liquid crystalline polymer (referred to herein as "LCP").

Also disclosed herein are methods of forming a coated microneedle array. Such methods generally include a step of providing a microneedle array. The step of providing the microneedle array can be accomplished by manufacturing the microneedle array, obtaining a microneedle array (for example by purchasing the microneedle array), or by some combination thereof.

Generally, an "array" refers to medical devices described herein that include more than one (in embodiments, a plurality) structure capable of piercing the stratum corneum to facilitate the transdermal delivery of therapeutic agents or the sampling of fluids through or to the skin. The terms "microstructure", or "microneedle" refer to the structures associated with an array that are capable of piercing the stratum corneum to facilitate the transdermal delivery of therapeutic agents or the sampling of fluids through or to the skin. By way of example, microstructures can include needle or needle-like structures as well as other structures capable of piercing the stratum corneum. The term "microneedle array" therefore can refer to a plurality of structures that are capable of piercing the stratum corneum to facilitate the transdermal delivery of therapeutic agents or the sampling of fluids through or to the skin.

Microneedle arrays useful in disclosed embodiments may include any of a variety of configurations, such as those described in the following patents and patent applications, the disclosures of which are incorporated herein by reference thereto. One embodiment for the microneedle arrays includes the structures disclosed in U.S. Patent Application Publication No. 2005/0261631 (the disclosure of which is incorporated herein by reference thereto), which describes microneedles having a truncated tapered shape and a controlled aspect ratio. A further embodiment for the microneedle arrays includes the structures disclosed in U.S. Pat. No. 6,881,203 (the disclosure of which is incorporated herein by reference thereto), which describes tapered microneedles with at least one channel formed on the outside surface. Another embodiment for the microneedle arrays includes the structures disclosed in U.S. Provisional Patent Application 61/168,268 (the disclosure of which is incorporated herein by reference thereto) and U.S. Provisional Patent Application 61/115,840 (the disclosure of which is incorporated herein by reference thereto), which both describe hollow microneedles.

Generally, a microneedle array can include a plurality of microneedles. FIG. 1 shows a portion of a microneedle array 200 that includes four microneedles 210 (of which two are referenced in FIG. 1) positioned on a microneedle substrate 220. Each microneedle 210 has a height h, which is the length from the tip of the microneedle 210 to the microneedle substrate 220. Either the height of a single microneedle or the average height of all microneedles on the microneedle array can be referred to as the height of the microneedle, h. In embodiments, each of the plurality of microneedles (or the average of all of the plurality of microneedles) can have a height of about 1 to 1200 micrometers (μm). In embodiments, each of the plurality of microneedles can have a height of about 1 to 1000 μm. In embodiments, each of the plurality of microneedles can have a height of about 200 to 750 μm.

A single microneedle or the plurality of microneedles in a microneedle array can also be characterized by their aspect ratio. The aspect ratio of a microneedle is the ratio of the height of the microneedle, h, to the width (at the base of the microneedle), w (as seen in FIG. 1). The aspect ratio can be presented as h:w. In embodiments, each of the plurality of microneedles (or the average of all of the plurality of microneedles can have an aspect ratio in the range of 2:1 to 5:1. In embodiments, each of the plurality of microneedles can have an aspect ratio of at least 2:1. In embodiments, each of the plurality of microneedles can have an aspect ratio of at least 3:1.

In embodiments, a microneedle or the plurality of microneedles in a microneedle array can also be characterized by their shape. In embodiments, each of the plurality of microneedles can have a square pyramidal shape or the shape of a hypodermic needle.

In embodiments a single microneedle or the plurality of microneedles in a microneedle array can also be characterized by its internal structure. In embodiments, each of the plurality of microneedles can have a cavity (for example a cylindrical cavity) extending the entire length of the microneedle (hollow microneedle), a cavity (for example a cylindrical cavity) extending through a portion of the microneedle (a partially hollow microneedle), or no internal cavity in the microneedle (solid microneedle). An internal cavity can provide a microneedle with additional surface area for coating the formulation and may allow for higher concentrations of API to be coated onto a microneedle.

Figure 2:
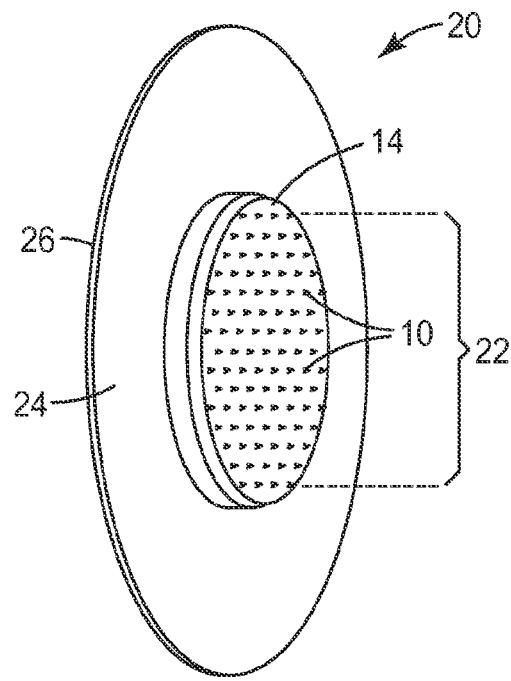
FIG. 2 is a schematic perspective view of a patch microneedle device.

In embodiments, a microneedle array may be applied to a skin surface in the form of a patch. Such an embodiment is shown in more detail in FIG. 2. FIG. 2 illustrates a device comprising a patch 20 in the form of a combination of a microneedle array 22, pressure sensitive adhesive 24 and backing 26. Such a patch 20, or a device including multiple microneedle arrays or multiple patches 20 can be referred to as a delivery device. A portion of the microneedle array 22 is illustrated with microneedles 10 protruding from a microneedle substrate 14. The microneedles 10 may be arranged in any desired pattern or distributed over the microneedle substrate 14 randomly. As shown, the microneedles 10 are arranged in uniformly spaced rows. In one embodiment, microneedle arrays can have a distal-facing surface area of more than about 0.1 cm$^2$ and less than about 20 cm$^2$; in embodiments more than about 0.5 cm$^2$ and less than about 5 cm$^2$. In one embodiment (not shown), a portion of the substrate 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 cm$^2$) to less than about 1 square inch (6.5 cm$^2$). In another embodiment (shown in FIG. 2), the microneedles are disposed over substantially the entire surface area of the array 22.

The next step in a disclosed method is to provide a coating substrate. One embodiment of a coating substrate within a larger system is shown in FIG. 3. A microneedle array 850 is provided having a microneedle substrate 820 and microneedles 830 extending from the microneedle substrate. A coating substrate 804 can be part of a coating reservoir block 802 that also includes walls 806. In embodiments, the coating substrate 804 may be a smooth metal surface. In another embodiment, the coating substrate 804 may be a thin, polymeric film or other flexible layer held against the top surface of the coating reservoir block 802. Other types of systems may also be utilized that include a coating substrate.

The next step includes providing an aqueous formulation as disclosed herein. The step of providing the aqueous formulation can be accomplished either by forming the aqueous formulation or by obtaining (via purchase or otherwise) a disclosed aqueous formulation. The aqueous formulation is applied to the coating substrate 804. As seen in FIG. 3, the aqueous formulation 810 is in contact with the coating substrate 804. The aqueous formulation 810 may be metered onto the coating substrate 804, such that the aqueous formulation has a desired thickness. Alternatively, an excess of aqueous formulation may be applied to the coating substrate 804 and the aqueous formulation can then be subsequently adjusted to the desired thickness by removing fluid with an edge device (such as a doctor blade). Other steps to apply a disclosed aqueous formulation to the coating substrate can also be utilized herein.

The next step in disclosed methods is to bring the aqueous formulation and the microneedles into contact with one another. This step can be accomplished by maintaining a position of the aqueous formulation and moving the microneedles relative to the aqueous formulation, by maintaining a position of the microneedles and moving the aqueous formulation relative to the microneedles, or by moving both the microneedles and the aqueous formulation. In embodiments, the step of bringing the aqueous formulation and the microneedles into contact with one another can further include bringing the microneedles into contact with the coating substrate 804. In embodiments, this can include contacting the microneedles (for example the tips of the microneedles) with the bottom surface of the coating substrate (for example a bottom surface of a coating well).

FIG. 3A illustrates an exemplary system for bringing the coating substrate and the microneedles into contact with one another. A flexible film 800 can be flexibly mounted to a rod 870 and can be part of a supporting assembly 860 that is held in place with an attachment band 872. The supporting assembly 860 can also include or be configured with a level compensator (not shown). In embodiments, a level compensator can function to ensure that the microneedles of the microneedle array make contact with the bottom of the coating well. As shown, the flexible film 800 can be supported by a pad 880 positioned between the rod 870 and the back of the flexible film 800. The back of the microneedle array 850 (i.e., the portion of the microneedle array opposed to the microneedles 830) can be attached to the flexible film 800. The microneedle array 850 is thus flexibly mounted to the supporting assembly 860.

FIG. 3B illustrates the exemplary system once the microneedles and the aqueous formulation have been brought into contact. The supporting assembly 860 and coating reservoir block 802 can be brought towards each other (either or both of the supporting assembly 860 and coating reservoir block 802 can be moved) such that the microneedle array 850 is brought into contact with the aqueous formulation 810. Other systems for contacting the aqueous formulation and the microneedles can also be utilized in disclosed methods.

The next step in disclosed methods can include removing the microneedles from the aqueous formulation. This step can be accomplished by maintaining a position of the aqueous formulation and moving the microneedles relative to the aqueous formulation, by maintaining a position of the microneedles and moving the aqueous formulation relative to the microneedles, or by moving both the microneedles and the aqueous formulation.

FIG. 3C illustrates the exemplary system once contact between the microneedles and the aqueous formulation has been terminated. The supporting assembly 860 can be removed from the coating reservoir block 802, thereby transferring at least a portion of the aqueous formulation 810 to the microneedle array 850. Some of the solvent in the aqueous formulation can then evaporate, thereby leaving a dried coating 815 on the microneedle array 850. The microneedle array 850 may be attached to the flexible film 800 by any conventional means, for example, by an adhesive bond or by a vacuum pulled through the flexible film 800 if the flexible film 800 is porous. In one embodiment, the microneedle array can be temporarily attached to the flexible film 800, such as by a low-strength, repositionable adhesive. In another embodiment, the microneedle array may be permanently attached to the flexible film 800 in the form of a patch as described above. The patch backing will thus serve as the flexible film 800 and may be temporarily attached to the supporting assembly 860, such as by a vacuum.

The step of contacting the aqueous formulation with the microneedles can be carried out more than once. For example, once the contact between the microneedles and the aqueous formulation has been terminated, the microneedles and the aqueous formulation can be brought into contact again. The optional second (and optional subsequent) steps of contacting the microneedles and the aqueous formulation can be carried out immediately, or there can be a delay between the contact steps.

The next step in disclosed methods can include removing residual solvents. This can be performed using various means including for example, drying at ambient conditions; drying at conditions other than ambient conditions (such as temperatures other than room temperature or a humidity other than an average humidity); drying for various times; drying with heat, lyophilization, freeze drying; other similar techniques; or combinations thereof.

Once at least a portion of the solvent from the aqueous formulation has evaporated (either from a single contact step or multiple contact steps), the aqueous formulation on the microneedle array can be referred to as a coating composition. The coating composition can include at least the at least one API from the aqueous formulation. Alternatively, the coating composition can include a portion of the at least one excipient from the aqueous formulation, a portion of the solvent (water and optional co-solvents) from the aqueous formulation, or some combination thereof. The content of the coating composition on the coated microneedle array can depend at least in part on the aqueous formulation, the method of coating the microneedle array, the number of contacting steps, other optional steps, length and quantities of delays between contacting steps, the speed of withdrawal from the reservoir, other factors not discussed herein, or some combination thereof.

Methods of coating microneedle arrays can be used to form coated microneedle arrays. A coated microneedle array can include a plurality of microneedles and a coating composition on at least a portion of the plurality of microneedles.

Microneedle devices may be used for immediate delivery, for example, application and immediate removal of the device from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

EXAMPLES

Materials

Bovine serum albumin (BSA) and lysozyme, chicken egg white, were purchased from Calbiochem (La Jolla, Calif.). Hydroxyethylcellulose (HEC) 100 cp; saccharin sodium dihydrate; L-Arginine HCl; sucrose; and Tween 80 were purchased from Spectrum Chemical (Gardena, Calif.). Ovalbumin was purchased from Sigma (St. Louis, Mo.). Plasdone® K90 and Plasdone® C17 were received from ISP Technologies (Wayne, N.J.). Albucult™, recombinant human serum albumin (rHSA), was received from Novozyme (Nottingham, UK). Dextran 60 was purchased form Pharmacosmos (Holbaek, Denmark). L-Lysine Monohydrate was purchased from Alpha Aesar (Ward Hill, Mass.). Phosphate buffered saline (PBS) (Ominpur grade, 10× concentrate) was purchased from EMD (Gibbstown, N.J.). The 10×PBS was diluted to 1×PBS with water from a Barnstead nanopure diamond purifier (Thermo Scientific, Waltham, Mass.).

Female Yorkshire pigs were obtained from Midwest Research Swine (Gibbon, Minn.). The weight of the animals used for the study ranged from 7 kg to 45 kg. The animals were quarantined and housed individually in solid bottom animal runs. The animal facility was accredited by the Association for Assessment and Accreditation of Laboratory Animal Care (AAALAC, Frederick, Md.) and all procedures were in accordance with an approved Institutional Animal Care and Usage Committee (IACUC) protocol.

The microneedle arrays prepared from polycarbonate (PC) (Lexan HPS1R-1125, GE Plastics, Pittsfield, Mass.) were injection molded according to the general description provided in International Patent Application Publication WO2005/082596. The microneedle arrays prepared from liquid crystalline polymer (LCP) (Vectra® MT1300, Ticona Plastics, Auburn Hills, Mich.) were injection molded according to the general description provided in U.S. Provisional Patent Application 61/287,799. The arrays were molded into a 1.27 cm² disk. The microneedles on the arrays had a square pyramidal shape with a needle height of approximately 500 microns and a tip-to-tip needle spacing of approximately 550 microns. The polycarbonate arrays were composed of approximately 366 microneedles and the LCP arrays were composed of approximately 316 microneedles.

Determination of Protein Concentration in Coating Formulations

The protein concentration of each coating formulation was verified by reverse-phase HPLC (RP-HPLC). Samples were prepared by diluting approximately 15 mcg of the coating formulation to an appropriate concentration with a solution of PBS containing 0.2 mg/mL Tween 80. The solutions were transferred to silanized HPLC autosampler vials (National Scientific, Rockwood, Tenn.) for analysis.

The amount of protein transferred to a microneedle array after dip coating was quantified by RP-HPLC. The coated composition was extracted from coated arrays by placing each coated array in a 5 mL low density polyethylene sample vial (Nalgene, Rochester, N.Y.) with the needles facing down. Depending on the expected amount of formulation on the array, 1-3 mL of PBS containing 0.2 mg/mL of Tween 80 was added to each vial. The vials were placed on an orbital shaker for approximately 30 minutes and the samples were transferred to silanized HPLC autosampler vials for analysis.

RP-HPLC analysis for BSA and ovalbumin was conducted using an Agilent 1100 chromatograph (Agilent Technologies, Santa Clara, Calif.) equipped with a solvent degasser, binary pump, thermostated autosampler, and diode array UV detector. The column was a Zorbax 300 SB-C8 (2.1×150 mm) with a 5 micron particle size (Agilent Technologies, Santa Clara, Calif.). The mobile phase A was composed of water with 0.1% trifluoroacetic acid (TFA) and mobile phase B was composed of methanol with 0.1% TFA. The system was programmed to deliver a gradient of 95/5 to 10/90 (A/B) over 2 minutes with the final conditions held for 30 seconds. The total run time was 5 minutes. The injection volume was 50 µL for BSA and 100 µL for ovalbumin. The flow rate was 1.0 mL/min, the column temperature was set at 60° C. and the detector measured absorbance at 215 nm. Chromatographic data were collected and processed using Empower software (Waters, Milford, Pa.). An external standard solution of each test compound was used for calibration and quantification.

RP-HPLC analysis for lysozyme and rHSA was conducted using an Agilent 1200 chromatograph (Agilent Technologies, Santa Clara, Calif.) equipped with a solvent degasser, binary pump, thermostated autosampler, and variable wavelength UV detector. The column was a Zorbax 300 SB-C8 (2.1×150 mm) with a 3.5 micron particle size. Mobile phase A was composed of water with 0.1% TFA and mobile phase B was composed of acetonitrile with 0.1% TFA. The system was programmed to deliver a gradient of 95/5 to 50/50 (A/B) over 5 minutes with the final conditions held for 30 seconds. The overall run time was 10 minutes. The injection volume was 20 mL, the flow rate was 0.5 mL/min, the column temperature was set at 65° C. and the detector measured absorbance at 200 nm. Chromatographic data were collected and processed using Empower software (Waters, Milford, Pa.). An external standard solution of each test compound was used for calibration and quantification.

Example 1

All coating formulations were prepared on a weight percent basis (w/w) and were prepared using 1×PBS unless otherwise stated. The fourteen coating formulations that were used to coat the microneedle arrays are listed in Table 1. Formulations 1 through 5, 10-14 were prepared by first dissolving the polymer component (Dextran, HEC or Plasdonone®) in PBS. After the polymer was completely dissolved, the non-protein excipients were added. The formulations were mixed until all of the solutes were dissolved. The protein was then added and the formulations were mixed until all of the protein was dissolved.

In Formulation 6 (Table 1), the order of solute addition was sucrose followed by BSA. The sucrose was completely dissolved prior to the addition of BSA. In Formulation 8 (Table 1) the Albult™, rHSA solution, was concentrated in the first step of the process. The Albult was concentrated approximately 3.5 fold to a concentration of 36% w/w using a Vivaspin 20 mL ultrafiltration spin column (30,000 MWCO PES) (Sartorius Stedim Biotech, Aubagne, France). The sample was centrifuged in the Vivaspin ultrafiltration spin column using a CS-69 centrifuge with a GH 3.8 swinging bucket rotor (Beckman Instruments, Brea, Calif.). The saccharin sodium dihydrate was added and completely dissolved before the addition of the lysozyme. The formulation was mixed until the lysozyme was completely dissolved and a homogeneous formulation was obtained.

In Formulations 7 and 9 no excipients were used. In Formulation 7 the BSA was added directly to the PBS and the contents were mixed until a homogeneous solution was obtained. In Formulation 9 the ovalbumin was added directly to the water and the contents were mixed until a homogeneous solution was obtained.

TABLE 1

| Formulation Number | Formulation |
|---|---|
| 1 | 11% BSA, 3% HEC, 50% sucrose |
| 2 | 8% BSA, 3% HEC, 50% sucrose, 5% tween 80 |
| 3 | 10% lysozyme, 3% HEC, 50% sucrose |
| 4 | 8% BSA, 11% Plasdone ® K90, 30% saccharin sodium dihydrate |
| 5 | 0.5% BSA, 5% HEC, 60% sucrose |
| 6 | 33% BSA, 30% sucrose |
| 7 | 37% BSA |
| 8 | 11% lysozyme, 20% rHSA, 30% saccharin sodium dihydrate |
| 9 | 20% ovalbumin in water |
| 10 | 9.5% BSA, 25% Dextran 60, 2% L-arginine HCl, 10% L-lysine monohydrate |
| 11 | 10% BSA, 40% Dextran 60 |
| 12 | 12% BSA, 30% Dextran 60, 3% L-arginine HCl |
| 13 | 10% BSA, 15% Plasdone ® C17, 30% saccharin sodium dihydrate, 5% propylene glycol |
| 14 | 10% BSA, 15% Plasdone ® C17, 30% saccharin sodium dihydrate, 5% glycerol |

Example 2

The viscosity of each coating formulation was measured on an AR-G2 stress rheometer (TA Instruments (New Castle, Del.) using 20 mm parallel plates. The measurements were performed at 25° C. and a shear rate of 100 s$^{-1}$. The test results are shown in Table 2.

TABLE 2

| Formulation Number | Formulation | Viscosity (cp) |
|---|---|---|
| 1 | 11% BSA, 3% HEC, 50% sucrose | 2970 |
| 2 | 8% BSA, 3% HEC, 50% sucrose, 5% tween 80 | 3270 |
| 3 | 10% lysozyme, 3% HEC, 50% sucrose | 2270 |
| 4 | 8% BSA, 11% Plasdone ® K90, 30% saccharin sodium dihydrate | 4850 |
| 5 | 0.5% BSA, 5% HEC, 60% sucrose | 7910 |
| 6 | 33% BSA, 30% sucrose | 828 |
| 7 | 37% BSA | 780 |
| 8 | 11% lysozyme, 20% rHSA, 30% saccharin sodium dihydrate | 222 |
| 9 | 20% ovalbumin in water | 47 |
| 10 | 9.5% BSA, 25% Dextran 60, 2% L-arginine HCl, 10% L-lysine monohydrate | 719 |
| 11 | 10% BSA, 40% Dextran 60 | 3590 |
| 12 | 12% BSA, 30% Dextran 60, 3% L-arginine HCl | 534 |
| 13 | 10% BSA, 15% Plasdone ® C17, 30% saccharin sodium dihydrate, 5% propylene glycol | 1916 |
| 14 | 10% BSA, 15% Plasdone ® C17, 30% saccharin sodium dihydrate, 5% glycerol | 518 |

Example 3

The contact angle of each coating formulation was measured on PC and LCP substrates using an optical drop shape analysis system (Model DSA 100S, KRÜSS, Hamburg, Germany) using Drop Shape Analysis (DSA) for Windows™ software version 1.90.0.14 (KRÜSS, Hamburg, Germany). The contact angle was calculated using the 'Sessile Drop Fitting' method in the DSA software. To perform the measurement, a 7 mcL droplet of coating formulation was transferred from a syringe (1 mL, 1.8 mm needle diameter) onto the substrate. Measurements were taken within 5 seconds of the transfer of the coating formulation onto the substrate. The angle between the liquid/solid interface and the tangent at the droplet interface was calculated by the DSA software using the Sessile Drop Fitting method. The contact angles reported were determined by taking the average of both measured angles. All measurements were made at ambient conditions, 23° C., 28% relative humidity (RH). For each formulation, the measurement procedure was conducted a total of five times and the contact angle was reported as the average value from the five measurements (Table 3).

TABLE 3

| Formulation Number | Formulation | Contact angle on PC (degrees) | Contact angle on LCP (degrees) |
|---|---|---|---|
| 1 | 11% BSA, 3% HEC, 50% sucrose | 84 | 81 |
| 2 | 8% BSA, 3% HEC, 50% sucrose, 5% tween 80 | 68 | 61 |
| 3 | 10% lysozyme, 3% HEC, 50% sucrose | 84 | 82 |
| 4 | 8% BSA, 11% Plasdone ® K90, 30% saccharin sodium dihydrate | 75 | 72 |
| 5 | 0.5% BSA, 5% HEC, 60% sucrose | 86 | 81 |
| 6 | 33% BSA, 30% sucrose | 85 | 83 |
| 7 | 37% BSA | 113 | 96 |
| 8 | 11% lysozyme, 20% rHSA, 30% saccharin sodium dihydrate | 63 | 57 |
| 9 | 20% ovalbumin in water | 81 | 74 |
| 10 | 9.5% BSA, 25% Dextran 60, 2% L-arginine HCl, 10% L-lysine monohydrate | 88 | 93 |
| 11 | 10% BSA, 40% Dextran 60 | 93 | 93 |
| 12 | 12% BSA, 30% Dextran 60, 3% L-arginine HCl | 94.42 | 87.84 |
| 13 | 10% BSA, 15% Plasdone ® C17, 30% saccharin sodium dihydrate, 5% propylene glycol | 71.08 | 62.98 |
| 14 | 10% BSA, 15% Plasdone ® C17, 30% saccharin sodium dihydrate, 5% glycerol | 74.40 | 61.28 |

Example 4

The surface tension of each coating formulation at the liquid/air interface was measured using an optical drop shape analysis system described above. The surface tension was calculated using the 'Pendant Drop Fitting' method in the DSA software. To take the measurement, a droplet of coating formulation was formed by dispensing 7 mcL of coating formulation from a syringe (1 mL, 1.8 mm needle diameter). The dispensed liquid droplet was suspended from the needle tip; the surface tension of the coating formulation at the liquid/air interface was calculated by the DSA software using the Pendant Drop Fitting method. All measurements were made at ambient conditions 23° C., 28% RH. Measurements were taken within 5 seconds of the formation of the coating formulation droplet. For each formulation, the measurement procedure was conducted a total of five times and the surface tension was reported as the average value from the five measurements (Table 4).

TABLE 4

| Formulation Number | Formulation | Surface tension (dynes/cm) |
|---|---|---|
| 1 | 11% BSA, 3% HEC, 50% sucrose | 48 |
| 2 | 8% BSA, 3% HEC, 50% sucrose, 5% tween 80 | 26 |

TABLE 4-continued

| Formulation Number | Formulation | Surface tension (dynes/cm) |
|---|---|---|
| 3 | 10% lysozyme, 3% HEC, 50% sucrose | 50 |
| 4 | 8% BSA, 11% Plasdone ® K90, 30% saccharin sodium dihydrate | 45 |
| 5 | 0.5% BSA, 5% HEC, 60% sucrose | 45 |
| 6 | 33% BSA, 30% sucrose | 52 |
| 7 | 37% BSA | 50 |
| 8 | 11% lysozyme, 20% rHSA, 30% saccharin sodium dihydrate | 40 |
| 9 | 20% ovalbumin in water | 55 |
| 10 | 9.5% BSA, 25% Dextran 60, 2% L-arginine HCl, 10% L-lysine monohydrate | 54 |
| 11 | 10% BSA, 40% Dextran 60 | 53 |
| 12 | 12% BSA, 30% Dextran 60, 3% L-arginine HCl | 38 |
| 13 | 10% BSA, 15% Plasdone ® C17, 30% saccharin sodium dihydrate, 5% propylene glycol | 37 |
| 14 | 10% BSA, 15% Plasdone ® C17, 30% saccharin sodium dihydrate, 5% glycerol | 45 |

Example 5

PC and LCP microneedle arrays, having a needle height of approximately 500 microns and a needle spacing of approximately 550 microns (measured apex to apex), were coated with the Formulations 1-11. The coating was done using a dip coating process in a controlled temperature and humidity environment (set points were 20° C. and 40% RH). The coating well, having a depth of approximately 240 microns, was chilled to approximately 10° C. with a Neslab RTE-111 water chiller (Thermo Scientific, Waltham, Mass.), throughout the coating process. An excess amount of formulation needed to fill the well was manually placed along the leading edge of the well. The formulation was then spread and leveled by passing an edge device across the top of the well. The arrays were individually dipped into the coating well. The arrays were held in place by vacuum located on an end of arm tooling fixture. Once mounted onto the fixture, the arrays were dipped one time into the leveled coating well. The level compensator, PIAB (Hingham, Mass.) with a spring load of 0.245 lbs. allowed for compression of the end of arm fixture and ensured that microneedles on the arrays contacted the bottom of the coating well. Upon removal from the coating well, the coated arrays were stored in a light and moisture proof foil pouch at 2-8° C.

The total amount of formulation [wet coating weight ($W_{CF}$)] transferred to the microneedle arrays by the dip coating method was calculated using Equation 1. The reported wet coating weight (mcg/array) was determined as the average of five individual measurements (Table 5).

$$W_{CF}(\text{mcg/array}) = \frac{C_{protein/array}(\text{mcg/array}) \times 100\%}{C_{protein/CF}(w/w\ \%)} \quad \text{Equation 1}$$

Where: $C_{protein/array}$=the amount of protein per array (mcg/array) as measured by RP-HPLC $C_{protein/CF}$=the amount of protein in the coating formulation as measured by RP-HPLC

TABLE 5

| Formulation Number | Formulation | Wet coating wt PC (mcg/array) | Wet coating wt LCP (mcg/array) |
|---|---|---|---|
| 1 | 11% BSA, 3% HEC, 50% sucrose | 307 | 249 |
| 2 | 8% BSA, 3% HEC, 50% sucrose, 5% tween 80 | 350 | 199 |
| 3 | 10% lysozyme, 3% HEC, 50% sucrose | 196 | 199 |
| 4 | 8% BSA, 11% Plasdone ® K90, 30% saccharin sodium dihydrate | 189 | 166 |
| 5 | 0.5% BSA, 5% HEC, 60% sucrose | 175 | 130 |
| 6 | 33% BSA, 30% sucrose | 331 | 233 |
| 7 | 37% BSA | 330 | 251 |
| 8 | 11% lysozyme, 20% rHSA, 30% saccharin sodium dihydrate | 401 | 351 |
| 9 | 20% ovalbumin in water | 1 | 2 |
| 10 | 9.5% BSA, 25% Dextran 60, 2% L-arginine HCl, 10% L-lysine monohydrate | 239 | 268 |
| 11 | 10% BSA, 40% Dextran 60 | 291 | 245 |
| 12 | 12% BSA, 30% Dextran 60, 3% L-arginine HCl | 205 | 183 |
| 13 | 10% BSA, 15% Plasdone ® C17, 30% saccharin sodium dihydrate, 5% propylene glycol | 328 | 271 |
| 14 | 10% BSA, 15% Plasdone ® C17, 30% saccharin sodium dihydrate, 5% glycerol | 281 | 216 |

Example 6

The distribution and location of each of the formulations transferred to the microneedle arrays during the dip coating process described in Example 5 was determined by optical microscopy. The distribution of the coating on the microneedles was visually determined using a Nikon Eclipse LV 100 optical microscope (Melville, N.Y.). The coated arrays were viewed at either 50 or 100× magnifications using bright field. The PC microneedle arrays were viewed using diascopic illumination. The LCP microneedle arrays were viewed using diascopic and episcopic illumination simultaneously. The microneedle arrays were positioned on the stage at an 80 degree angle with the microneedles facing up. For reporting purposes a uniform distribution of formulation was defined as an array in which all of the microneedles in an array were coated with approximately the same amount of formulation. The distribution of coating on the microneedles for Formulations 1-8, 10-14 was uniform across each individual array. For Formulations 1-8, 10-14 the location of the coating on the microneedles was found to be on the top half of each microneedle. The microneedle arrays coated with Formulation 9 were coated with so little of the coating formulation that a uniform coating could not be determined

Example 7

A determination of the relative amount of protein released from the dip coated microneedle arrays was quantified using an in vivo release study in female Yorkshire pigs. The animals were sedated with ketamine (10 mg/kg) and then anesthetized with isoflurane gas administered through a nose mask. The anesthetized swine were transferred to a heating pad and the hams were shaved with Oster Clippers (McMinnville, Tenn.) using a 50 blade. Next shaving cream was applied to the skin and the skin was shaved with a flat razor. After the skin was wet shaved, the site was rinsed with water and cleaned with isopropyl alcohol. The skin was allowed to dry for 5 minutes prior to patch application. The patch application sites were chosen to be free of blemishes and nicks.

Each microneedle array used in the study was patched after the dip coating procedure. Each array was patched by physically attaching the back of the array to a 5 cm² adhesive patch with 1513 double-sided medical adhesive (3M Company, St. Paul, Minn.). The patched array was placed in an injection molded polycarbonate application collar and the assembly was stored in a light and moisture proof pouch until just prior to the time of application.

The coated microneedle arrays were applied to the prepared skin using a spring-loaded applicator. The spring-loaded applicator provided an impact velocity of 8.4 m/s to the patched array sitting in the application collar. At the completion of a 5 minute wear time, the patches were removed and the residual protein was extracted from the arrays in order to quantify the remaining protein. A mass balance calculation was used to determine the amount of protein released to the animal. The percent protein released was calculated by normalizing the amount of protein delivered by the initial amount of protein loaded onto the patch. The percent of protein released for each formulation was reported as the average value from five individual arrays (Table 6).

TABLE 6

| Formulation Number | Formulation | Protein Release from PC (%) | Protein Release from LCP (%) |
|---|---|---|---|
| 1 | 11% BSA, 3% HEC, 50% sucrose | 79 | 85 |
| 2 | 8% BSA, 3% HEC, 50% sucrose, 5% tween 80 | 83 | 88 |
| 3 | 10% lysozyme, 3% HEC, 50% sucrose | 81 | 85 |
| 4 | 8% BSA, 11% Plasdone ® K90, 30% saccharin sodium dihydrate | 90 | 90 |
| 5 | 0.5% BSA, 5% HEC, 60% sucrose | NA | NA |
| 6 | 33% BSA, 30% sucrose | 82 | 80 |
| 7 | 37% BSA | 66 | 71 |
| 8 | 11% lysozyme, 20% rHSA, 30% saccharin sodium dihydrate | Not tested | Not tested |
| 9 | 20% ovalbumin in water | NA | NA |
| 10 | 9.5% BSA, 25% Dextran 60, 2% L-arginine HCl, 10% L-lysine monohydrate | 95 | 96 |
| 11 | 10% BSA, 40% Dextran 60 | 95 | 94 |
| 12 | 12% BSA, 30% Dextran 60, 3% L-arginine HCl | 95 | 95 |
| 13 | 10% BSA, 15% Plasdone ® C17, 30% saccharin sodium dihydrate, 5% propylene glycol | 77 | 82 |
| 14 | 10% BSA, 15% Plasdone ® C17, 30% saccharin sodium dihydrate, 5% glycerol | 76 | 76 |

NA: in vivo release data could not be determined because protein levels were below the limit of quantification.

Thus, embodiments of AQUEOUS FORMULATIONS FOR COATING MICRONEEDLE ARRAYS are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A method of forming a coated microneedle array comprising providing a microneedle array comprising a microneedle substrate and a plurality of microneedles; providing a coating substrate; providing an aqueous formulation comprising at least one active pharmaceutical ingredient and at least one excipient, wherein the aqueous formulation has a viscosity of from 500 to 30,000 centipoise when measured at a shear rate of 100 s$^{-1}$ and a temperature of 25° C.; applying the aqueous formulation to the coating substrate; bringing the aqueous formulation and the microneedles of the microneedle array into contact with one another; removing the microneedles from the aqueous formulation; and allowing at least a portion of the aqueous formulation to evaporate, wherein the aqueous formulation has a contact angle on a medical grade polymeric material of 50° or greater and 96° or less when measured under ambient conditions.

2. The method according to claim 1, wherein the viscosity is from 500 to 10,000 centipoise when measured at a shear rate of 100 s$^{-1}$ and a temperature of 25° C.

3. The method according to claim 1, wherein the viscosity is from 500 to 8,000 centipoise when measured at a shear rate of 100 s$^{-1}$ and a temperature of 25° C.

4. The method according to claim 1, wherein the aqueous formulation has a contact angle on a medical grade polymeric material of 65° or greater and 96° C. or less when measured under ambient conditions.

5. A method of forming a coated microneedle array comprising providing a microneedle array comprising a microneedle substrate and a plurality of microneedles; providing a coating substrate; providing an aqueous formulation comprising at least one active pharmaceutical ingredient and at least one excipient, wherein the aqueous formulation has a contact angle on a medical grade polymeric material of 50° or greater and 96° or less when measured under ambient conditions; applying the aqueous formulation to the coating substrate; bringing the aqueous formulation and the microneedles into contact with one another; removing the microneedles from the aqueous formulation; and allowing at least a portion of the aqueous formulation to evaporate.

6. The method according to claim 5, wherein the aqueous formulation has a contact angle on a medical grade polymeric material of 65° or greater and 96° C. or less when measured under ambient conditions.

7. The method according to claim 1, wherein the at least one active pharmaceutical ingredient is selected from vaccines, proteins, peptides, and polynucleotide sequences.

8. The method according to claim 1, wherein the at least one excipient comprises a buffer selected from histidine, phosphate buffers, acetate buffers, citrate buffers, glycine buffers, ammonium acetate buffers, succinate buffers, pyrophosphate buffers, Tris acetate (TA) buffers, Tris buffers, saline solutions buffered with any of the above, or combinations thereof.

9. The method according to claim 1, wherein the at least one excipient comprises sucrose, dextrins, dextrans, hyroxyethyl cellulose (HEC), polyvinyl pyrrolidone (PVP), polyethylene glycols, amino acids, polysorbate, human serum albumin, ethanol, sodium chloride, EDTA, saccharin sodium dehydrate, or combinations thereof.

10. The method according to claim 1, wherein the active pharmaceutical ingredient is a vaccine and the aqueous formulation further comprises one or more adjuvants.

11. The method according to claim 1, wherein the material comprising the microneedle array is selected from polycarbonate and liquid crystalline polymer.

12. The method according to claim 1, wherein the coating substrate is at least a portion of a coating well.

13. The method according to claim 12, wherein the coating well comprises a bottom surface and the microneedles contact the bottom surface of the coating well.

14. The method according to claim 1, wherein the step of applying the aqueous formulation to the coating substrate comprises applying an excess of aqueous formulation to the coating substrate and adjusting the amount of aqueous formulation on the coating substrate.

15. The method according to claim 14, wherein the step of adjusting the amount of aqueous formulation on the coating substrate comprises removing some aqueous formulation using an edge device.

16. The method according to claim 1, wherein the step of bringing the aqueous formulation and the microneedles of the microneedle array into contact with one another is repeated at least once.

17. The method according to claim 1, wherein the aqueous formulation has a surface tension that is from 40 and 55 dynes/cm when measured under ambient conditions.

* * * * *

UNITED STATES PATENT AND TRADEMARK OFFICE
CERTIFICATE OF CORRECTION

PATENT NO. : 9,693,950 B2  
APPLICATION NO. : 13/699805  
DATED : July 4, 2017  
INVENTOR(S) : Amy S. Determan Page 1 of 2

It is certified that error appears in the above-identified patent and that said Letters Patent is hereby corrected as shown below:

In the Specification

Column 1,
Line 8, "PCT/038029," should read --PCT/US2011/038029,--.

Column 2,
Line 47, "hyroxyethyl" should read --hydroxyethyl--.

Column 4,
Line 46, "hyroxyethyl" should read --hydroxyethyl--.

Column 6,
Line 45, "hyroxyethyl" should read --hydroxyethyl--.

Column 8,
Line 49, "hyroxyethyl" should read --hydroxyethyl--.

Column 9,
Line 66, "hyroxyethyl" should read --hydroxyethyl--.

Column 11,
Line 20, "hyroxyethyl" should read --hydroxyethyl--.

Column 12,
Lines 35-36, "iospropanol," should read --isopropanol,--.
Lines 36-37, "dimethysulfoxide," should read --dimethylsulfoxide,--.
Line 37, "2-pryrrolidinone," should read --2-pyrrolidinone,--.
Line 38, "dimethylformamide" should read --dimethylformamide.--.
Line 56, "pamedronate;" should read --pamidronate;--.

Signed and Sealed this  
Twenty-second Day of May, 2018

Andrei Iancu  
*Director of the United States Patent and Trademark Office*

Column 13,
Line 13, "polysaccharides," should read --polysaccharides--.
Line 13, "oligosaccharides," should read --oligosaccharides--.
Line 50, "leutinizing" should read --luteinizing--.
Line 53, "leutinizing" should read --luteinizing--.
Line 54, "goanadotropns" should read --gonadotropins--.
Line 56, "adrenocortiocotropic" should read --adrenocorticotropic--.

Column 14,
Line 39, "momosacharides" should read --monosaccharides--.
Line 52, "pregelanitized" should read --pregelatinized--.
Line 54, "clyclodextrin," should read --cyclodextrin,--.
Line 54, "clyclodextrin," should read --cyclodextrin,--.
Lines 54-55, "clyclodextrin," should read --cyclodextrin,--.

Column 15,
Line 21, "serubem" should read --serine,--.
Line 22, "agrinine," should read --arginine,--.
Line 48, "iospropanol," should read --isopropanol,--.
Line 49, "dimethysulfoxide," should read --dimethylsulfoxide,--.
Line 50, "pryrrolidinone," should read --pyrrolidinone,--.
Line 66, "digylcolide" should read --diglycolic--.

Column 24,
Line 25, "20 mL," should read --20 μL--.
Lines 40-41, "Plasdonone®" should read --Plasdone®--.

Column 28,
Line 54, "determined" should read --determined.--.

In the Claims

Column 30,
Lines 61-62, in Claim 9, "hyroxyethyl" should read --hydroxyethyl--.